US006790635B1

(12) United States Patent
Seiki et al.

(10) Patent No.: US 6,790,635 B1
(45) Date of Patent: Sep. 14, 2004

(54) METHOD FOR RESTENOSIS FOLLOWING CORONARY VESSEL INTERVENTION

(75) Inventors: Kosuke Seiki, Ibaraki (JP); Hiroshi Oda, Tokyo (JP); Hiroshi Nakajima, Saitama (JP); Nobuyuki Sato, Ibaraki (JP); Yoshihiro Urade, Kyoto (JP); Yoshio Uehara, Tokyo (JP); Teruo Inoue, Saitama (JP)

(73) Assignees: Maruha Corporation (JP); Japan Science and Technology Corporation (JP); Osaka Bioscience Institute (JP)

( * ) Notice: Subject to any disclaimer, the term of this patent is extended or adjusted under 35 U.S.C. 154(b) by 0 days.

(21) Appl. No.: 09/914,319

(22) PCT Filed: Feb. 25, 2000

(86) PCT No.: PCT/JP00/01109

§ 371 (c)(1),
(2), (4) Date: Aug. 24, 2001

(87) PCT Pub. No.: WO00/50898

PCT Pub. Date: Aug. 31, 2000

(30) Foreign Application Priority Data

Feb. 26, 1999 (JP) ............................................ 11-051216

(51) Int. Cl.[7] ............................ C12Q 1/26; G01N 33/53
(52) U.S. Cl. ................................ 435/25; 435/7.1; 435/4
(58) Field of Search ................................ 435/4, 7.1, 25, 435/7.92, 7.9, 7.91, 810, 975

(56) References Cited

U.S. PATENT DOCUMENTS 5,807,828 A * 9/1998 Scarborough
6,461,827 B1 * 10/2002 Oda et al.

FOREIGN PATENT DOCUMENTS

EP 0999447 A1 10/2000 ......... G01N/33/573
WO WO 98/49559 * 11/1998

OTHER PUBLICATIONS

Urade, Yoshihiro et al.; "Secretion of lipocalin–type prostaglandin D synthase (beta.—trace) from human heart to plasma during coronary circulation" Adv. Exp. Med. Biol. (1999); 469 (Eicosanoids and other Bioactive Lipids I Cancer, Inflammation, and Radiation Injury, 4). 49–54; XP001038167.

Expression of lipocalin–type prostaglandin D synthase ($\beta$–trace in human heart and its accumulation in the coronary circulation of angina patients; Proc. Natl. Acad. Sci. USA vol. 94, No. 26 (1997) p. 14689–14694.

* cited by examiner

*Primary Examiner*—Leon B. Lankford, Jr.
*Assistant Examiner*—Ruth A. Davis
(74) *Attorney, Agent, or Firm*—Fish & Richardson P.C.

(57) ABSTRACT

The present invention provides a method for predicting restenosis following coronary intervention by measuring human lipocalin-type prostaglandin D synthase (L-PGDS) in a body fluid sample. More particularly, this method comprises measuring the L-PGDS concentration in the sample and predicting restenosis following coronary intervention by using a change therein as an indicator.

22 Claims, 4 Drawing Sheets

METHOD FOR RESTENOSIS FOLLOWING CORONARY VESSEL INTERVENTION

FIELD OF THE INVENTION

The present invention relates to a method for predicting restenosis following coronary intervention by measuring a human lipocalin-type prostaglandin D synthase (hereinafter referred to as L-PGDS) concentration in a body fluid sample. More particularly, the invention relates to the method for predicting restenosis following coronary intervention using changes in the L-PGDS concentration in the sample as an indicator.

BACKGROUND OF THE INVENTION

Methods for treating an ischemic heart disease such as angina, which brings about stenosis in a coronary, include pharmacotherapy, coronary artery bypass graft, and coronary intervention.

Pharmacotherapy is a basic treatment for angina, and is used for improving myocardinal ischemic conditions. Its mechanism of action works in two ways: one expands a coronary artery, improving a bloodflow into the myocardium (e.g. nitrous acid), and the other decreases the heart rate and blood pressure to reduce oxygen consumption of the myocardium, thereby preventing the occurrence of an attack (e.g. β blocker agent). On the other hand, coronary artery bypass graft is a method in which a blood vessel is newly established for a stenosed part to connect the aorta with peripheries of the stenosed part in a coronary artery, thereby reconstructing the circulation of the coronary artery.

Coronary intervention is a method in which an intravascular catheter is inserted into a femoral artery and directed to a stenosed part, and then a physical treatment is performed locally to ensure blood flow. Various devices are used in coronary intervention. A Percutaneous Transluminal Coronary Angioplasty (referred to as PTCA hereinafter) is a method in which a balloon catheter is inserted into a blood vessel and expanded in a stenosed part, thereby enlarging the stenosed part to recover a normal bloodflow. A coronary stent implantation is a method in which a metal wire-woven tube is implanted in a stenosed part using a catheter to support a lumen of the coronary artery, thereby ensuring a normal bloodflow.

As described above, coronary intervention is not accompanied by a surgical operation such as thoracotomy. Therefore, ever since Gruentig performed the first successful PTCA in 1977, it has become widely used in Japan, not to mention Europe and America. In the early days, the application of coronary intervention was limited to stable angina with a restricted lesion in a single vessel. Its application was then extended to a stable angina with lesions in multiple vessels, and further, to an angina with a complete obstruction. Nowadays, it has become one of the established treatments for ischemic heart diseases. However, there is a significant weak point in PTCA in that an acute and subacute thrombotic occlusion occurs in an early stage following the operation, and that restenosis occurs within 3 to 4 months at 30–40% probability (Nobuyoshi, M. et al. (1988) *Am. Coll. Cardiol.* 12: 616–623).

Among these, for the acute and subacute thrombotic occlusion which occurs at an early stage, a method in which an intracoronary stent is used as a device, and in addition, aspirin and ticlopidine are used together, has been established as a typical prevention (Lincoff, A. M. et al. (1993) *J. Am. Coll. Cardiol.* 21: 866–875).

On the other hand, a step towards solving the restenosis problem was also presented by the development of the intracoronary stent. The restenosis occurrence following intervention in cases where this device is used decreased to 20–30% compared to PTCA using a balloon. Later on, the advent of various stents greatly lowered the probability of restenosis, however, they have fallen short of completely preventing restenosis (Fishman, D. L. et al. (1994) *N. Engl. J. Med.* 331: 496–501; Serruys, P. W. et al. (1994) *N. Engl. J. Med.* 331: 489–501).

Therefore, together with the improvement of such devices, prevention by medication has also been attempted.

Since the restenosis is triggered by platelets accumulating toward an intimal injury caused by coronary intervention as well as the growth of a newly-born intima, and by a platelet-derived growth factor being produced, the effect of antiplatelets was expected. However, none of aspirin, dipyridamole, and ticlopidine could reduce the restenosis occurrence. Furthermore, trapidil, which is an antagonist of the platelet-derived growth factor, was of no effect, and the preventive efficacy of anticoagulants, heparin and warfarin, was not confirmed either. Still further, it was reported that the restenosis rate is higher in the case of coronary spastic angina, and in view of the cause-effect relationship between restenosis and coronary spastic angina, the effect of a calcium antagonist was prospected. However, neither diltiazem nor nifedipine was effective (*Arteriosclerosis*: 122; Medical Aoi Press).

Under such circumstances, drugs that are being recognized as effective for restenosis have recently appeared. It has been reported that drugs that were prescribed as a keloidal drug such as tranilast which is an antiallergic agent and cilostazol which is an antiplatelet agent showed favorable results after PTCA, and basic research concerning these drugs is now proceeding (Ishiwata (1996) Kowa medical report Vol. 39, No. 3: 127–33; Tamal H. et al. (1994) *Circulation* 90: I-652; Katsuki et al. (1998) *Medicina* 35: 659–661). Although neither drug has been clinically tested on a large-scale yet, it is considered certain that effective drugs including these will emerge in the future.

Thus, an early prediction of the occurrence of restenosis will enable an effective precaution to be taken using drugs. Therefore, a method for early prediction of occurrence of restenosis following coronary intervention has been long expected, however, early prediction is not easy since restenosis following the intervention often occurs asymptomatically.

Nowadays, various factors involved in restenosis are being studied, and their relationship with the mechanism of restenosis is being examined. Since the plasma concentration of angiotensin converting enzyme is correlated with the amount of intimal growth following a stent placement, its potential as an indicator for predicting restenosis has been suggested (Ohishi (1995) *Hypertension* 26: 561). Furthermore, based on the assumption that a constrictive remodeling is involved in occurrence of restenosis following PTCA, studies on endothelin (referred to as ET hereinafter) which is a vasoactive substance having a strong vasoconstrictive effect, have been carried out. Doi et al. measured the ET concentration in a coronary artery before/after/three months after PTCA, and reported that a group with significant stenosis showed a greater degree of changes in the concentration compared to a group without significant stenosis was not confirmed, and they reported clinical data indicating that the ET increase in the coronary circulation played an important role in the mechanism of coronary artery restenosis following PTCA (*Journal of Cardiology* vol. 32 Supplement 1: p391). It is suggested that the platelet-derived growth factor also has a potential as a factor for predicting restenosis in view of its involvement in a restoration process after being damaged by PTCA (Haneo et al. (1993) *Journal of Clinical* and *Experimental Medicine* 167 No. 6 p512). Naruko et al. carried out an investigation on the expression of natriuretic peptide system in a restenosed part, and confirmed the expression of natriuretic peptide C, natriuretic peptide A receptor, and natriuretic peptide clearance receptor in a newly-born intima of the restenosed part (*Journal of Japan Atherosclerosis society* vol. 25 Supplement 1998: 140).

However, for each agent excepting ET, the data merely indicates its involvement in the mechanism of restenosis, and no clinical findings capable of predicting restenosis at an early stage after coronary intervention have been obtained so far. Additionally, since ET requires a long-term follow-up of the changes in the concentration, it is not practical from the viewpoint of early prediction under present circumstances.

Furthermore, several investigations have also been carried out on a method for predicting restenosis using an apparatus. Among the dynamics of coronary circulation during PTCA, a collateral blood flow ratio at the time of coronary occlusion [(QC/QN) max=coronary artery wedge pressure/average arterial pressure], that is to say, a collateral circulation upon coronary occlusion with balloon expansion during PTCA, was measured upon completion of PTCA, and its relationship with subsequently occuring restenosis was examined. As a result, it is reported that the degree of (QC/QN) max and restenosis are closely related (*Journal of Cardiology* vol. 32 Supplement I: P393).

Kikuchi et al. showed that the transition of QTd and QTcd before coronary intervention, on the day following the intervention, in the period immediately after the intervention (5–24 days), and in the chronic period (69–204 days) using a 12 inducible electrocardiogram in the resting state after the intervention can be used as an indicator for predicting restenosis (*Journal of Cardiology* vol. 32 Supplement I: p394).

However, these methods are not suitable for an early prediction since, on the one hand, (QC/QN) max is invasive because it is accompanied by an intracardiac catheter method, while on the other hand, the transition of QTd and QTcd requires a considerable period of time for measurement.

As mentioned above, although various investigations on a method for predicting restenosis following coronary intervention simply, non-invasively and promptly have been carried out, an outstanding predicting method that overcomes these problems has not been reported yet.

On the other hand, we found that it is possible to detect and predict ischemic diseases using a L-PGDS concentration as an indicator since the L-PGDS concentration in a great cardiac vein and peripheral bloods of an angina patient is significantly higher than that of a healthy person. Further, it is possible to manage a prognosis of angina following PTCA, that is, to judge whether the stenosis is preferably eliminated by PTCA or not, since the L-PGDS concentration in great cardiac vein blood after PTCA decreases to the level of a healthy person at the convalescence stage (wo98/49559). However, its relevance with restenosis following coronary intervention has been unexamined.

The object of the present invention is to provide a method for predicting the restenosis which may occur after coronary intervention simply, non-invasively, and promptly, the method being outstanding in that no burden is placed on a patient having difficulties in a coronary angiography such as an elderly person, kidney-diseased patient, etc.

SUMMARY OF THE INVENTION

To solve the above problems, we studied extensively and intensively as to whether a L-PGDS concentration can be a factor for predicting restenosis. Specifically, the L-PGDS concentration in a body fluid sample following coronary intervention was traced and its relevance with restenosis was examined. As a result, serial changes in the L-PGDS concentration in the sample after the intervention or changes before/after the intervention were divided into 2 types: 1) Type where the concentration decreased once after the intervention, then subsequently increased up until 48 hours after the intervention; 2) Type where the concentration decreased once after the intervention, and subsequently showed almost no change up until 48 hours after the intervention. It was found that this type-division could be used to classify patients into those in which restenosis would occur later and those in which no restenosis would occur. That is to say, it was elucidated that restenosis occurs a few months later in the case where no increase in the L-PGDS concentration in a body fluid sample has been observed at an early stage after the intervention, while on the other hand, no restenosis occurs in the case where the increase in the L-PGDS concentration has been observed. Accordingly, tracing the serial changes in the L-PGDS concentration in a body fluid sample enabled the prediction of the occurrence of restenosis following coronary intervention.

Thus, the present invention provides a method for predicting restenosis following coronary intervention wherein the L-PGDS concentration in a body fluid sample is measured after the intervention, or before and after the intervention, and the changes in its value are used as an indicator, the method providing the following items (1)–(7):

(1) A method for predicting restenosis following coronary intervention by measuring a L-PGDS concentration in a body fluid sample;

(2) The method of the above (1) wherein a serial change in the L-PGDS concentration in the body fluid sample after coronary intervention is used as an indicator;

(3) The method of the above (1) wherein a change in the L-PGDS concentration in the body fluid sample between before and after coronary intervention is used as an indicator;

(4) The method of the above (1) wherein the L-PGDS concentration in the body fluid sample is measured using an immunological measuring method;

(5) The method of the above (1) wherein the body fluid sample is blood or urine;

(6) The method of the above (5) wherein the body fluid sample is blood taken from a coronary or peripheral blood; and (7) The method of the above (1) wherein coronary intervention is percutaneous transluminal coronary angioplasty (PTCA), directional coronary atherectomy (DCA), transluminal extraction catheter (TEC), rotary atherectomy coronary angioplasty (Rotablator), excimer laser coronary angioplasty, or intracoronary stenting.

The specification of the present invention includes part or all of the contents as described in the specification and/or drawings of Japanese Patent Application No. 11-51216, which is a priority document of the present application.

BEST MODE FOR CARRYING OUT THE INVENTION

The present invention will be described in detail.

Coronary intervention includes, but is not limited to, operations that have a possibility of later restenosis occurrence such as percutaneous transluminal coronary angioplasty (PTCA), directional coronary atherectomy (DCA), transluminal extraction catheter (TEC), rotary atherectomy coronary angioplasty (Rotablator), excimer laser coronary angioplasty, intracoronary stenting, etc.

In the present invention, a sample for which a L-PGDS concentration is measured, is a body fluid sample taken from a subject, for example, blood, urine, etc.

A method for measuring the L-PGDS concentration in the above sample may be an immunological measuring method, an enzyme activity measuring method, etc., but it is not particularly limited as long as the measuring method reflects the L-PGDS concentration accurately. However, at an actual clinical site, an immunological measuring method such as EIA, ELISA, RIA, FIA, etc. using monoclonal or polyclonal antibodies that are specific to L-PGDS is preferred in view of its simplicity and the necessity of measuring a large amount of samples simultaneously.

Of the above-mentioned immunological measuring methods, a sandwich ELISA method using a L-PGDS specific monoclonal antibody is particularly preferred. Said monoclonal antibody includes, for example, an antibody produced by hybridoma cell strains, such as 1B7 (FERM BP-5709, deposited on Sep. 21, 1995), 7F5 (FERM BP-5711, deposited on Jun. 6, 1996), 6F5 (FERM BP-5710, deposited on Sep. 21, 1995), 9A6 (FERM BP-5712, deposited on Jun. 6, 1996) and 10A3 (FERM BP-5713, deposited on Jun. 6, 1996), those strains being deposited in the National Institute of Bioscience and Human-Technology (1-1-3, Higashi, Tsukuba, Tbaraki, Japan).

When performing measurement with the sandwich ELISA method, a L-PGDS detection kit containing the above monoclonal antibody, which we have already established, can be used (see WO97/16461).

In the present invention, restenosis following coronary intervention can be predicted using the L-PGDS concentration measured by the above method as an indicator.

For the purpose of predicting restenosis following the intervention, a change over time in the L-PGDS concentration value in a body fluid sample of a subject measured by the above method is traced after the intervention, or before and after the intervention. Specifically, the case where the L-PGDS concentration hardly increases at an early stage after the intervention, i.e. within 48 hours, is judged as positive, and thus prediction can be performed. "Hardly increases" as used herein means that the ratio of the L-PGDS concentration in the sample does not exceed a specified ratio at two points after the intervention or at two points before and after the intervention, that is, for example, immediately before the intervention and 48 hours after the intervention. Changes in the concentration can be also judged by the concentration comparison or serial concentration change patterns at the following points: for example, immediately before the intervention and 24 hours after the intervention; immediately after the intervention and 24 hours after the intervention; immediately after the intervention and 48 hours after the intervention; and 24 hours after the intervention and 48 hours after the intervention. Thus, the method for observing changes in the concentration is not particularly limited as long as serial changes in the concentration are shown by the method.

EXAMPLES

Embodiments of the present invention will be described below by means of illustration, but it is not intended that the scope of the present invention is limited to these embodiments.

Example 1

Measurement Over Time of a L-PGDS in Coronary Blood Following a PTCA-1

For blood taken from a coronary at points before and after PTCA (at four points: before PTCA; immediately after PTCA; 24 hours after PTCA; and 48 hours after PTCA) in the case of isolated left anterior descending coronary artery disease, a L-PGDS concentration was measured by a sandwich ELISA method using two types of antibodies.

(1) Creation of the Standard Curve

An anti L-PGDS monoclonal antibody capable of binding with the L-PGDS (clone: 7F5) was diluted in 50 mM carbonic acid buffer (pH 9.6) to the concentration of 4.4 $\mu$g/ml, subsequently added to a 96-well microtiter plate by 300 $\mu$l per well, and then left to stand overnight at 4° C. for solidification. This plate was washed with phosphate buffer saline (pH 7.4, referred to as PBS hereinafter) three times, then 300 $\mu$l of PBS containing 0.2% casein (pH 7.4, referred to as blocking solution hereinafter) was added to each well, and the plate was subsequently incubated for 90 min at 30° C., thus performing blocking.

Next, the plate after blocking was washed with PBS containing 0.05% Tween20 (referred to as T-PBS hereinafter) three times, then 100 $\mu$l of a standard L-PGDS solution (prepared by serial dilution of L-PGDS refined from cerebrospinal fluid with the blocking solution) was added to each well, followed by incubation for 90 min at 30° C. After reaction, the plate was washed with T-PBS three times, then 100 $\mu$l of horseradish peroxidase-labeled anti-PGDS monoclonal antibody (clone: 1B7) diluted with the blocking solution to 0.5 $\mu$g/ml was added to each well, followed by incubation for 90 min at 30° C. After washing three times with T-PBS, 100 $\mu$l of coloring solution (ABTS solution: manufactured by Boehringer Mannheim) was added to each well, followed by incubation for 30 min at 30° C. Subsequently, the reaction was stopped by adding 100 $\mu$l of stop solution (1.5% oxalic acid) to each well, and stirring with a plate mixer. The difference of absorbance at 405 nm and 490 nm (A405 nm–490 nm) was measured by a commercially available plate reader (model number Sk601, manufactured by SEIKAGAKU CORPORATION), thereby creating the standard curve.

The monoclonal antibody (clone: 1B7, 7F5) used in the above sandwich ELISA method was obtained (3–10 mg/ml) by means of: injecting 1.0 ml pristane into a mouse intraperitoneally; then at the second week, implanting $1 \times 10^8$ of each antibody producing cell strain into the peritoneal cavity of the mouse; collecting ascites two weeks later; and subjecting the obtained ascites to protein A affinity column chromatography.

The names of the above-mentioned monoclonal antibody producing cell strains are consistent with those of the above-mentioned monoclonal antibodies, respectively, and each cell strain is deposited in the National Institute of Bioscience and Human-Technology (1-1-3, Higashi, Tsukuba, Ibaragi, Japan) under FERM BP-5709 (deposited on Sep. 21, 1995) for 1B7 and FERM BP-5711 (deposited on Jun. 6, 1996) for 7F5.

(2) Measurement of the L-PGDS Concentration in a Body Fluid Sample

The collected blood was diluted as appropriate with the blocking solution, and the L-PGDS concentration thereof was measured according to the above sandwich ELISA method.

Figure 1:
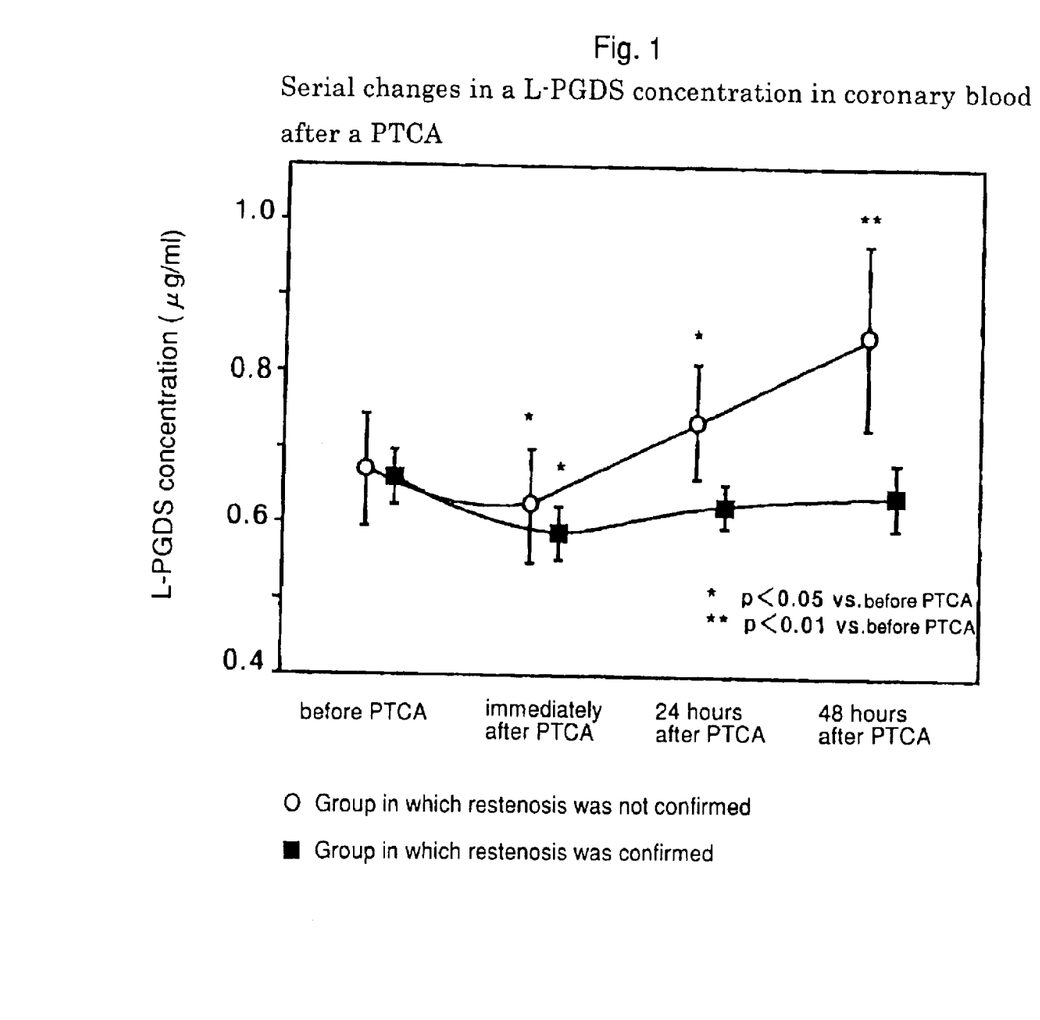
FIG. 1 is a graph showing serial changes in the L-PGDS concentration in a coronary blood after a PTCA.

Meanwhile, the cases of 24 subjects were classified into two groups: one group for cases with restenosis (n=10) and one for cases without restenosis (n=14). Restenosis was determined by quantitative coronary angiography (QCA) using a CAM-1000 (PSP Corp) three months after the PTCA, and the group with significant restenosis was defined as those subjects with a restenosis rate of not less than 50%. From the changes over time in the L-PGDS concentration of each group, it was elucidated that the two groups showed different patterns to each other (FIG. 1). That is to say, in the group without restenosis, the concentration decreased once immediately after PTCA, and subsequently showed a tendency to increase over time at 24 and 48 hours after PTCA. In contrast, in the group with restenosis, the concentration decreased once immediately after PTCA, and showed almost no increase thereafter. Thus, a statistically significant difference was clearly confirmed between the two groups.

Further, for all 24 cases, the ratio (A/B) of the L-PGDS concentration 48 hours after PTCA (A) to the L-PGDS concentration before PTCA (B) was determined, and those values were compared for the two groups classified by the above criteria. As a result, the ratio (A/B) of the group without restenosis was 1.22±0.31 (average±standard deviation, and the same applies hereinafter), and the ratio of the group with restenosis was 1.01±0.09; thus a statistically significant difference was confirmed between those two groups (P<0.005). Similarly, the ratios (C/B) of the L-PGDS concentration 24 hours after PTCA (C) to the L-PGDS concentration before PTCA (B) was 1.06±0.12 for the group without restenosis and 1.00±0.10 for the group with restenosis; the ratios (A/D) of the L-PGDS concentration 48 hours after PTCA (A) to the L-PGDS concentration immediately after PTCA (D) was 1.42±0.28 for the group without restenosis and 1.04±0.13 for the group with restenosis; the ratios (C/D) of the L-PGDS concentration 24 hours after PTCA (C) to the L-PGDS concentration immediately after PTCA (D) was 1.26±0.23 for the group without restenosis and 1.02±0.12 for the group with restenosis; and the ratios (A/C) of the L-PGDS concentration 48 hours after PTCA (A) to the L-PGDS concentration 24 hours after PCA (C) was 1.14±0.18 for the group without restenosis and 1.02±0.09 for the group with restenosis. Thus, with respect to the ratio of concentration at any point, a significant difference between the two groups was confirmed.

Example 2

Measurement Over Time of L-PGDS in Coronary Blood After a PTCA-2

In 10 cases of isolated left anterior descending coronary artery disease, a L-PGDS concentration was measured by a sandwich ELISA method using two types of antibodies for blood taken from a coronary before and after PTCA (at two points: before PTCA, and 48 hours after PTCA). Subsequently, the above 10 cases were classified by the ratio of the L-PGDS concentration 48 hours after PTCA to the L-PGDS concentration before PTCA as described in Example 1. Of these, the cases in which the ratio was above 1.10 (average of the group with restenosis+standard deviation) were classified as a group in which an increase in the blood concentration was confirmed, and the cases in which the ratio was not more than 1.10 were classified as a group in which no change was confirmed. The results are shown in FIG. 2.

Figure 2:
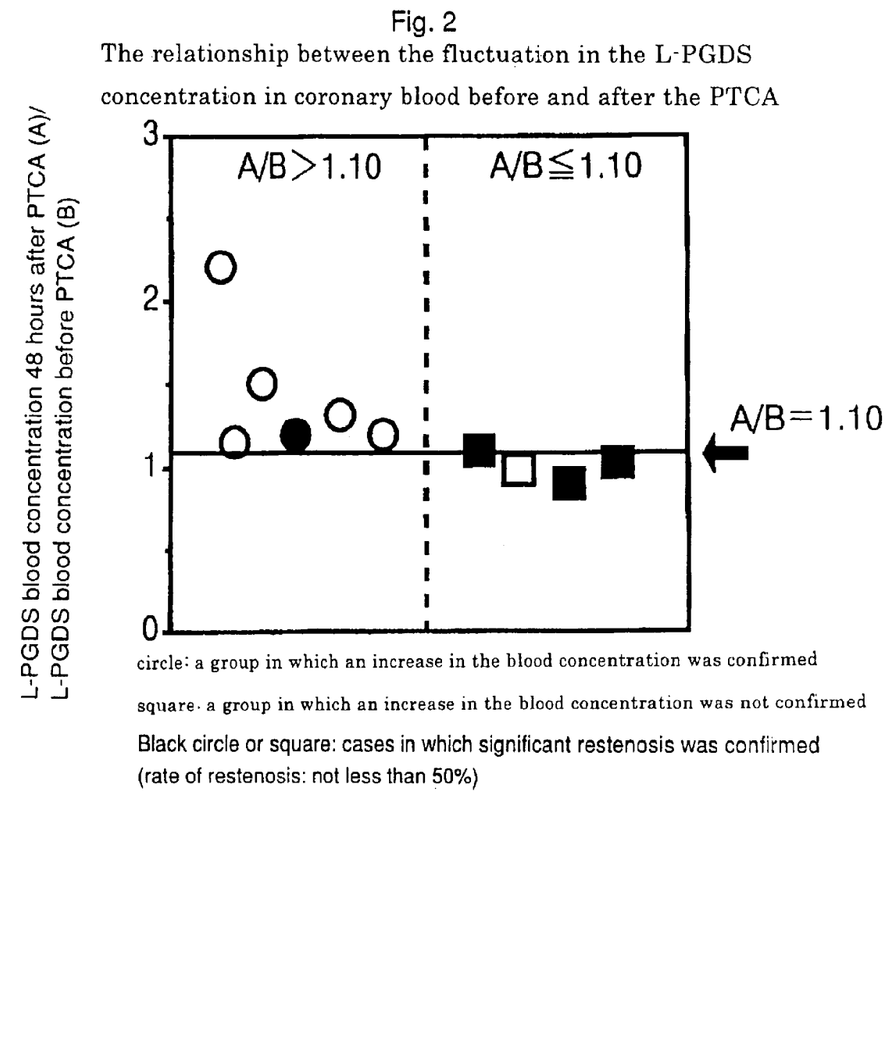
FIG. 2 is a graph showing the relationship between the fluctuation in the L-PGDS concentration in a coronary blood before and after a PTCA.

As shown in FIG. 2, there were six cases in which the L-PGDS concentration increased after PTCA with respect to the concentration before PTCA (marked as a circle in the figure) and four cases in which no increase was confirmed (marked as a square in the figure). The occurrence of restenosis was examined for each subject three months after the operation in the same manner as in Example 1. The results showed that one case (16.7%) out of the 6 in which the L-PGDS concentration had increased had significant resenosis (marked in black in the figure), and three cases (75%) out of the 4 in which the L-PGDS concentration had not increased had significant restenosis. Thus, a difference in the occurrence of restenosis between the two groups was confirmed.

Example 3

Measurement Over Time of L-PGDS in Peripheral Blood After a PTCA-3

In a case of isolated left anterior descending coronary artery disease, a L-PGDS concentration was measured by a sandwich ELISA method using two types of antibodies for blood taken from peripheries at points before and after PTCA (at four points: before PTCA; immediately after PTCA; 24 hours after PTCA; and 48 hours after PTCA).

Figure 3:
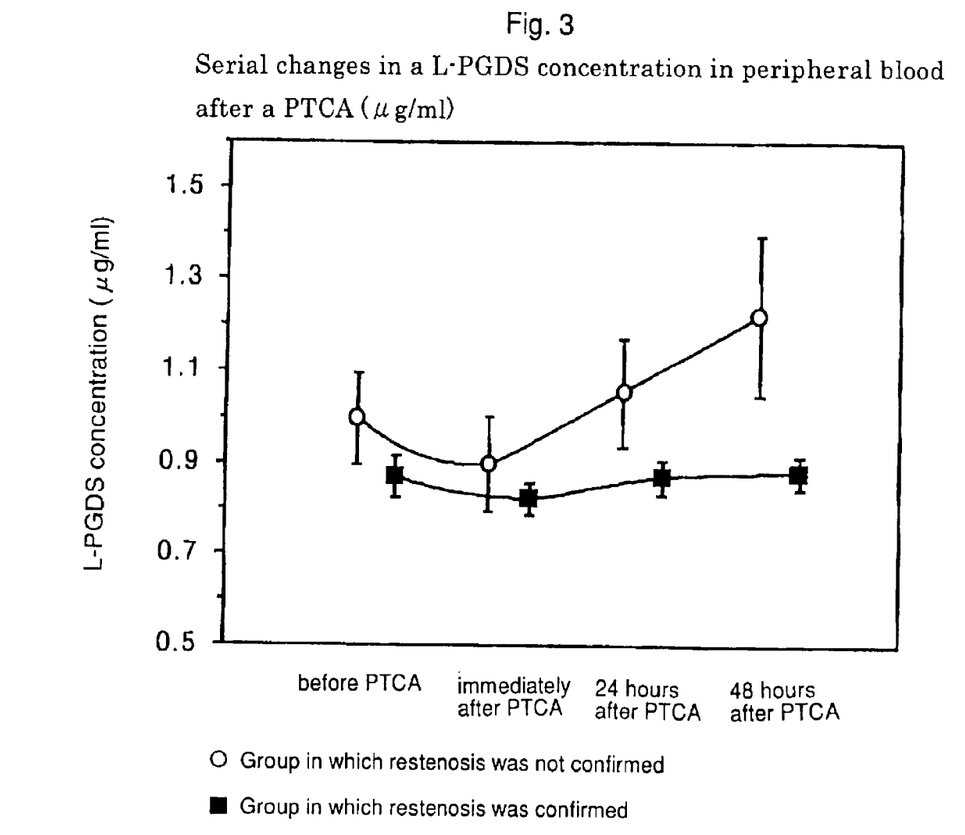
FIG. 3 is a graph showing serial changes in the L-PGDS concentration in peripheral blood after a PTCA.

Meanwhile, the cases of 24 subjects were classified into two groups: one group for cases with restenosis (n=10) and one for cases without restenosis (n=14) in the same manner as in Example 1. The method for determining the occurrence of restenosis was in accordance with the method described in Example 1. From the changes over time in the L-PGDS concentration in each group, it was elucidated that the two groups showed different patterns to each other (FIG. 3). That is to say, in the group without restenosis, the concentration decreased once immediately after PTCA, and subsequently showed a tendency to increase over time at 24 and 48 hours after PTCA. In contrast, in the group with restenosis, the concentration decreased once immediately after PTCA and showed almost no increase thereafter. Thus, a statistically significant difference was clearly confirmed between the two groups, similar to the tendency confirmed in the coronary blood.

In the same manner as in Example 1, for all 24 cases, the ratio (A/B) of the L-PGDS concentration 48 hours after PTCA (A) to the L-PGDS concentration before PTCA (B) was determined, and those values were compared for the two groups classified by the above criteria. The results showed that the ratio (A/B) was 1.23±0.29 for the group without restenosis and 1.03±0.14 for the group with restenosis; thus a statistically significant difference between the two groups was confirmed (P<0.005). Similarly, the ratio (C/B) of the L-PGDS concentration 24 hours after PTCA (C) to the L-PGDS concentration before PTCA (B) was 1.10±0.16 for the group without restenosis and 1.02±0.15 for the group with restenosis; the ratio (A/D) of the L-PGDS concentration 48 hours after PTCA (A) to the L-PGDS concentration immediately after PTCA (D) was 1.32±0.35 for the group without restenosis and 1.08±0.14 for the group with restenosis; the ratio (C/D) of the L-PGDS concentration 24 hours after PTCA (C) to the L-PGDS concentration immediately after PTCA (D) was 1.17±0.20 for the group without restenosis and 1.07±0.16 for the group with restenosis; and the ratio (A/C) of the L-PGDS concentration 48 hours after PTCA (A) to the L-PGDS concentration 24 hours after PTCA (C) was 1.11±0.13 for the group without restenosis and 1.02±0.07 for the group with restenosis. Thus, with respect to the ratio of concentration at any point, a significant difference between the two groups was confirmed.

Example 4

Measurement Over Time of L-PGDS in Peripheral Blood After a PTCA-4

In 12 cases of of isolated left anterior descending coronary artery disease, a L-PGDS concentration was measured by a sandwich ELISA method using two types of antibodies for blood taken from peripheries before and after PTCA (at two points: before PTCA, and 48 hours after PTCA). Subsequently, the above 12 cases were classified by the ratio of the L-PGDS concentration 48 hours after PTCA to the L-PGDS concentration before PTCA as described in Example 3. Of these, the cases in which the ratio was above 1.17 (average of group with restenosis+standard deviation) were classified as a group in which an increase in the concentration was confirmed, and the cases in which the ratio was not more than 1.17 were classified as a group in which no change was confirmed. The results are shown in FIG. 4.

Figure 4:
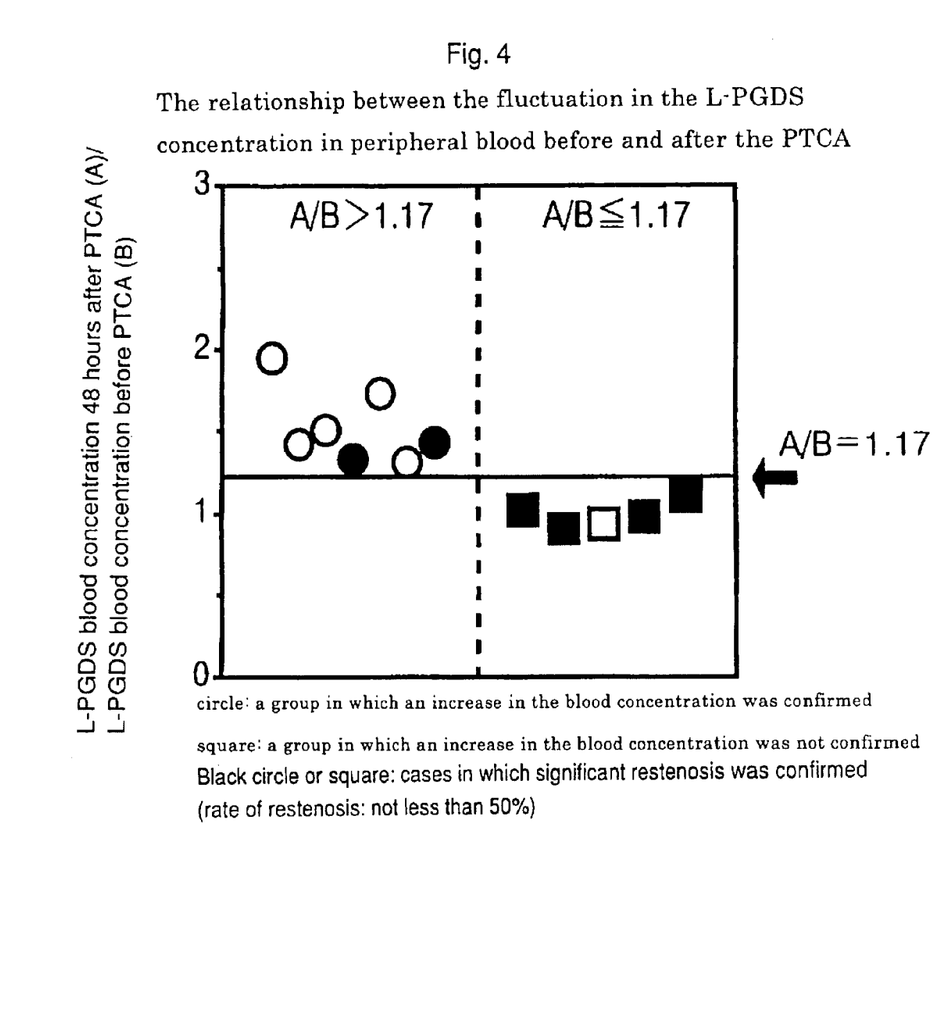
FIG. 4 is a graph showing the relationship between the fluctuation in the L-PGDS concentration in peripheral blood before and after a PTCA.

As shown in FIG. 4, there were seven cases in which the L-PGDS concentration increased after PTCA with respect to the concentration before PTCA (marked as a circle in the figure) and five cases in which no increase was confirmed (marked as a square in the figure). The occurrence of restenosis was examined for each subject three months after the operation in the same manner as in Example 1. The results showed that two cases (28.6%) out of the seven in which the L-PGDS concentration had increased had significant restenosis (marked in black in the figure) and four cases (80%) out of the five in which the L-PGDS concentration had not increased had significant restenosis. Thus, a difference in the occurrence of restenosis between the two groups was confirmed.

As seen from the above results, it was elucidated that restenosis can be predicted by detecting the degree of change in the L-PGDS concentration following coronary intervention.

INDUSTRIAL APPLICABILITY

When restenosis occurs after coronary intervention, additional intervention must be performed to treat it. This places a significant financial and physical burden on a patient. It is possible to predict restenosis non-invasively and simply at an earlier stage, which can only be diagnosed invasively now. The present invention also facilitate more effective prevention by drugs now being tested. Furthermore, the present invention will enable the prediction of restenosis with reduced burden on a patient having difficulties in coronary angiography such as an elderly patient, a kidney-deseased patient, etc.

All publications, patent and patent applications cited herein are incorporated herein by reference in their entirety.

What is claimed is:

1. A method for predicting restenosis following coronary intervention, the method comprising:

measuring a lipocalin-type prostaglandin D synthase (L-PGDS) concentration in a body fluid sample extracted from a subject at least twice between immediately before the coronary intervention and 48 hours after the intervention; and predicting that restenosis does not develop when the L-PGDS concentration increases within 48 hours after the intervention and that restenosis does develop when the L-PGDS concentration does not increase within 48 hours after the intervention.

2. The method of claim 1 wherein the L-PGDS concentration is measured at least twice within 48 hours after the coronary intervention.

3. The method of claim 2, wherein the L-PGDS concentration is measured immediately after the coronary intervention and at 24 hours after the coronary intervention.

4. The method of claim 2, wherein the L-PGDS concentration is measured immediately after the coronary intervention and at 48 hours after the coronary intervention.

5. The method of claim 2, wherein the L-PGDS concentration is measured at 24 hours after the coronary intervention and at 48 hours after the coronary intervention.

6. The method of claim 1 wherein the L-PGDS concentration is measured once before and at least once after the coronary intervention.

7. The method of claim 6, wherein the L-PGDS concentration is measured immediately before the coronary intervention and at 24 hours after the coronary intervention.

8. The method of claim 6, wherein the L-PGDS concentration is measured immediately before the coronary intervention and at 48 hours after the coronary intervention.

9. The method of claim 1 wherein the L-PGDS concentration in the body fluid sample is measured using an immunological measuring method.

10. The method of claim 1 wherein the body fluid sample is blood or urine.

11. The method of claim 10 wherein the body fluid sample is blood taken from a coronary or peripheral blood.

12. The method of claim 1 wherein coronary intervention is percutaneous transluminal coronary angioplasty (PTCA), directional coronary atherectomy (DCA), transluminal extraction catheter (TEC), rotary atherectomy coronary angioplasty (Rotablator), excimer laser coronary angioplasty, or intracoronary stenting.

13. The method of claim 1 wherein the L-PGDS concentration is measured at least once before and once after the coronary intervention.

14. The method of claim 1 wherein, when the L-PGDS concentration increases within 48 hours after the intervention, the L-PGDS concentration decreases immediately after the intervention and then increases within 48 hours after the intervention.

15. The method of claim 1 wherein the L-PGDS concentration is measured immediately before the coronary intervention and at 48 hours after the coronary intervention.

16. The method of claim 1 wherein the L-PGDS concentration is measured immediately before the coronary intervention, immediately after the coronary intervention, and at 24 hours and 48 hours after the coronary intervention.

17. A method for predicting restenosis in a subject following coronary intervention, the method comprising comparing a lipocalin-type prostaglandin D synthase (L-PGDS)

concentration in a first sample of a body fluid to a L-PGDS concentration in a second sample of the body fluid, wherein the first sample is extracted from the subject between immediately before the intervention and 24 hours after the intervention and the second sample is extracted from the subject between 24 hours after the intervention and 48 hours after the intervention, and wherein, if the concentration in the second sample is higher than that in the first sample, then restenosis is predicted not to occur.

18. The method of claim 17, wherein the first and second samples are extracted from coronary blood and the concentration in the second sample is increased 10% or more relative to the concentration in the first sample.

19. The method of claim 17, wherein the first and second samples are extracted from the peripheral blood and the concentration in the second sample is increased 17% or more relative to the concentration in the first sample.

20. A method for predicting restenosis in a subject following coronary intervention, the method comprising:

collecting a first sample and a second sample of a body fluid between 24 hours after the intervention and 48 hours after the intervention; and comparing a lipocalin-type prostaglandin D synthase (L-PGDS) concentration in the first sample and in the second sample, wherein, if the concentration in the second sample is higher than that in the first sample, then restenosis is predicted not occur.

21. The method of claim 20, wherein the first and second samples are extracted from coronary blood and the concentration in the second sample is increased 10% or more relative to the concentration in the first sample.

22. The method of claim 20, wherein the first and second samples are extracted from the peripheral blood and the concentration in the second sample is increased 17% or more relative to the concentration in the first sample.

* * * * *

UNITED STATES PATENT AND TRADEMARK OFFICE
CERTIFICATE OF CORRECTION

PATENT NO. : 6,790,635 B1
DATED : September 14, 2004
INVENTOR(S) : Kosuke Seiki et al.

It is certified that error appears in the above-identified patent and that said Letters Patent is hereby corrected as shown below:

<u>Title page,</u>
Item [54], Title, should read -- METHOD FOR PREDICTING THE OCCURRENCE OF RESTENOSIS FOLLOWING CORONARY INTERVENTION --.

Signed and Sealed this

Seventh Day of March, 2006

JON W. DUDAS
*Director of the United States Patent and Trademark Office*